United States Patent
Kast et al.

(10) Patent No.: US 7,220,280 B2
(45) Date of Patent: May 22, 2007

(54) SPREADER IMPLANT FOR PLACEMENT BETWEEN VERTEBRAE

(75) Inventors: Erich Kast, Pfungen (CH); Hans-Joachim Wilke, Dornstadt (DE); Peter Weiland, Nonnweiler-Braunshausen (DE)

(73) Assignee: Advanced Medical Technologies AG, Nonnweiler-Braunshausen (DE)

( * ) Notice: Subject to any disclaimer, the term of this patent is extended or adjusted under 35 U.S.C. 154(b) by 0 days.

(21) Appl. No.: 10/686,039

(22) Filed: Oct. 15, 2003

(65) Prior Publication Data

US 2004/0127994 A1    Jul. 1, 2004

(30) Foreign Application Priority Data

Oct. 16, 2002    (DE)    ............... 102 48 170

(51) Int. Cl.
*A61F 2/44*    (2006.01)

(52) U.S. Cl. .................................. 623/17.11

(58) Field of Classification Search ............. 623/17.11, 623/17.14, 17.15, 17.16, 18.11, 23.47, 23.58; 606/60, 61, 63, 90, 105
See application file for complete search history.

(56) References Cited

U.S. PATENT DOCUMENTS

| | | | | |
|---|---|---|---|---|
| 3,765,296 A | * | 10/1973 | Fischer | 411/49 |
| 3,941,028 A | * | 3/1976 | Lobello et al. | 411/55 |
| 4,863,476 A | * | 9/1989 | Shepperd | 623/17.15 |
| 5,094,577 A | * | 3/1992 | Clark et al. | 411/64 |
| 5,489,210 A | * | 2/1996 | Hanosh | 433/173 |
| 5,522,899 A | * | 6/1996 | Michelson | 606/61 |
| 5,554,191 A | * | 9/1996 | Lahille et al. | 623/17.11 |
| 5,653,763 A | * | 8/1997 | Errico et al. | 623/17.11 |
| 5,665,122 A | * | 9/1997 | Kambin | 623/17.16 |
| 6,102,950 A | * | 8/2000 | Vaccaro | 623/17.16 |
| 6,190,414 B1 | * | 2/2001 | Young et al. | 623/17.15 |
| 6,193,757 B1 | * | 2/2001 | Foley et al. | 623/17.16 |
| 6,368,351 B1 | * | 4/2002 | Glenn et al. | 623/17.15 |
| 6,443,989 B1 | * | 9/2002 | Jackson | 623/17.15 |
| 6,773,460 B2 | * | 8/2004 | Jackson | 623/17.15 |
| 2003/0028249 A1 | * | 2/2003 | Baccelli et al. | 623/17.11 |

* cited by examiner

*Primary Examiner*—Todd E. Manahan
*Assistant Examiner*—David Comstock
(74) *Attorney, Agent, or Firm*—Friedrich Kueffner

(57) ABSTRACT

An implant for placement between vertebrae, with two sidepieces joined together at one end, each of which can be placed against one of the vertebrae, and with a device for vertical distraction of the sidepieces. In the initial position for the distraction, the outside surfaces of the sidepieces that face the vertebrae converge towards the free ends of the sidepieces. This wedge shape of the implant facilitates the insertion of the implant into the intervertebral space.

5 Claims, 2 Drawing Sheets

SPREADER IMPLANT FOR PLACEMENT BETWEEN VERTEBRAE

BACKGROUND OF THE INVENTION

The invention relates to an implant for placement between vertebrae, with two sidepieces joined together at one end, each of which can be placed against one of the vertebrae, and with a device for vertical distraction of the sidepieces.

Implants of this type are used after diskectomies to join the affected vertebrae. The implant serves primarily as a spacer to fill the intervertebral space previously filled by the disk. Since the implant, which is preferably provided with openings, is subsequently infiltrated by bony tissue, in which it becomes embedded, it also has a joining function. The implant promotes the formation of the bony tissue joining the vertebral bodies.

Implants of the aforementioned type are used principally in regions of the spine in which the facing end surfaces of the vertebral bodies are inclined towards each other. The implant inserted in the intervertebral space is spread, which causes the implant to adapt to the end surfaces of the vertebral bodies that are inclined towards each other.

SUMMARY OF THE INVENTION

The object of the present invention is to provide an implant of the aforementioned type that can be handled more easily than previously known implants of this type.

Pursuant to this object, and others which will become apparent hereafter, one aspect of the present invention resides in an implant in which, in the initial position for the distraction, the outside surfaces of the sidepieces facing the vertebrae converge towards the free ends of the sidepieces.

The wedge shape of the implant in its initial position advantageously facilitates the insertion of the implant into the intervertebral space.

It is advantageous for the joined sidepieces to be made from a single piece of plastic material that can be deformed for the distraction. An example of a suitable material for this purpose is polyetheretherketone (PEEK) or even titanium. It is advantageous for the slider, which, in its end position, in which the sidepieces are spread, remains in the implant as a spacer between the sidepieces, also to be made of this plastic material, which has a high load-bearing capacity.

In one embodiment, the invention provides that the facing inside surfaces of the sidepieces converge at least in stages towards the free ends of the sidepieces.

This embodiment with the inside surfaces of the sidepieces converging at least in stages allows the use of a spreading device formed only by a slider that can be moved between the sidepieces, which, when moved in the direction of the free ends of the sidepieces, fits against the converging inner surfaces of the sidepieces and thus spreads the sidepieces apart.

It is advantageous for the slider to be flush with the outer surface of the implant in the end position described above, i.e., for it to fit the outer contours of the implant without forming a recess between the sidepieces.

In the preferred embodiment of the invention, the implant is intended for placement in a lateral half-space of an intervertebral space to be filled after a diskectomy. To join the vertebrae, two implants of this type with mirror symmetry with respect to each other are needed. Advantageously, narrow implants of this type can be implanted with relatively little effort by a dorsal approach through the vertebral canal that skirts the spinal cord.

It is advantageous for the end of the implant opposite the free ends of the sidepieces to have an opening through which a tool can be passed, especially for manipulating the slider.

In another advantageous embodiment of the invention, the slider locks in place in its end position. It is advantageous to provide a releasable locking mechanism, which allows temporary reversal of the spreading, e.g., for the purpose of more exact positioning of the implant between the vertebrae.

It is advantageous for the outlines of the implant to have the general form of a rectangular solid. However, especially the sides facing the vertebrae may be adapted to the shape of the facing vertebral surfaces. The implant can have a height maximum in the direction from front to back, while the height becomes less from the middle of the vertebra to the lateral margin of the vertebra.

The various features of novelty, which characterize the invention, are pointed out with particularity in the claims annexed to and forming part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE INVENTION

Figure 1:
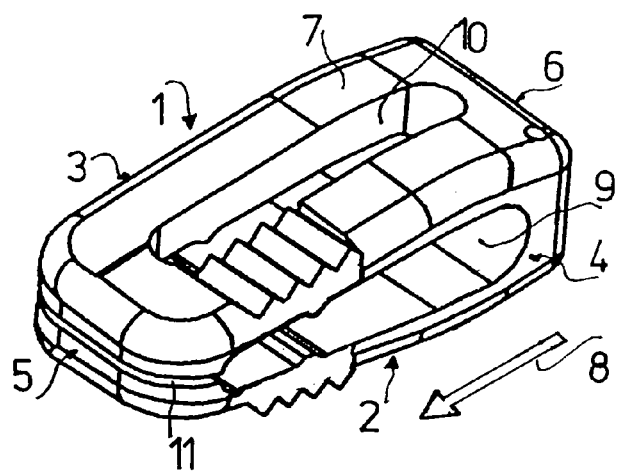
FIG. 1 shows a perspective view of an incomplete spreadable implant in accordance with the invention.

The implant shown in the drawings, which has the general form of a rectangular solid, has an upper side 1, a lower side 2, longitudinal sides 3,4 and end faces 5,6. The corners and edges of the implant are rounded.

In the embodiment shown here, the implant is made of polyetheretherketone (PEEK).

The shape of the implant deviates from a rectangular solid in that the height of the implant increases from the end face 5 towards the end face 6 to a maximum 7 and then declines again. The maximum height is located in the last third of the distance between the two end faces 5,6.

In another departure from the shape of a rectangular solid, the height of the implant decreases slightly from the longitudinal side 3 to the longitudinal side 4. Symmetry exists only with respect to a horizontal plane intersecting the implant in the middle of its maximum height.

The implant serves the purpose of filling a lateral half-space between two vertebral bodies. An implant with mirror symmetry with respect to this implant would be implanted in the opposite half-space. The implant is implanted in the direction of the arrow 8 by a dorsal approach through the vertebral canal that skirts the spinal cord.

The implant has a horizontal opening 9 and a vertical opening 10, such that the openings 9,10, which have the form of oblong holes, intersect. A slot recess 11, which opens inwardly to the openings 9,10, is provided on the end face 5.

Vertically movable sidepieces 12,13 are formed by the vertical opening 10 and the slot recess 11. The sidepieces 12,13 are connected to each other by a web 14 on the end face 6.

The web 14 has a bore 15 with a slot counterbore 16. The bore 15 opens inwardly both to the horizontal opening 9 and to the vertical opening 10.

In addition to the bore 15, another bore 17 perpendicular to it is formed in the web 14 for holding a metal pin. Teeth 18 are provided on the upper side and the lower side of the implant. The teeth 18 have ridges that extend transversely to the longitudinal direction of the implant from the longitudinal side 4 to the vertical opening 10.

A slider 19, which serves as a spreading element, is located between the sidepieces 12,13, flush with the longitudinal sides 3,4 of the implant. The slider 19, like the piece of material that forms the sidepieces 12,13 and the web 14, is formed as a single piece of PEEK.

A pilot pin 20 extends from the upper side of the slider 19, and another pilot pin 20 extends from the lower side of the slider 19. The two pilot pins 20 fit into the upper and lower parts of the vertical opening 10.

When the slider 19 is moved towards the free ends of the sidepieces 12,13, it comes to rest against converging, opposing inside surfaces 21,22 of the sidepieces 12,13. A catch 23 projects from each of the inside surfaces 21,22.

Figure 3:
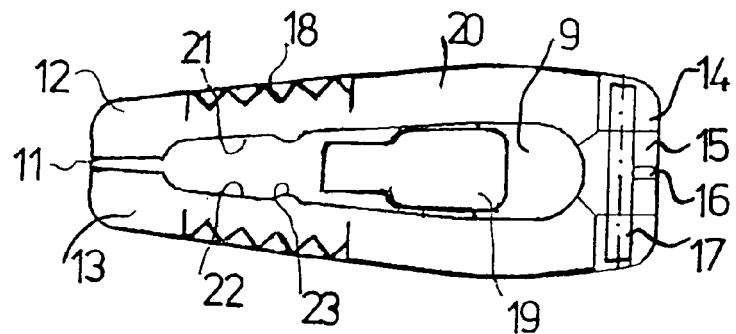
FIG. 3 shows a side view of the complete implant of FIG. 2 in the unspread state.

During implantation, the slider 19 is initially located approximately in the position shown in FIG. 3. The piece of material that forms the sidepieces 12,13 and the web 14 is undeformed in this initial state. The sidepieces 12,13 form a blunt wedge, which facilitates insertion of the implant into the space between two vertebrae.

Figure 2:
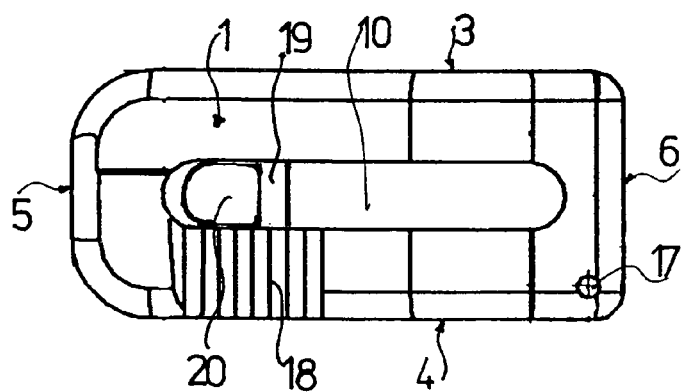
FIG. 2 shows a top view of the implant of FIG. 1 with the addition of a spreading element.

In the implanted position between the vertebrae, the slider 19 is moved towards the free ends of the sidepieces 12,13 by a tool that is passed through the bore 15 and possibly engages the slot counterbore, such that the slider 19, which fits against the converging inside surfaces 21,22 in such a way that it can slide, spreads the sidepieces 12,13 apart. As can be seen especially in FIG. 2, the lateral surfaces of the pilot pins 20 rest against the inside wall of the vertical opening 10, so that the slider 19 is guided without torsion between the sidepieces 12,13.

Figure 4:
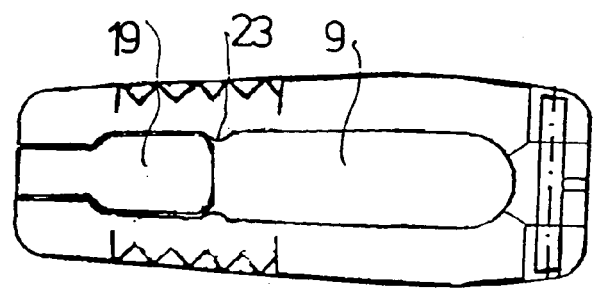
FIG. 4 shows a side view of the implant of FIG. 3 in the spread state.

In the end position shown in FIG. 4, the slider 19 is locked in place behind the catches 23. In this position, the slider 19 is flush with the outer surface of the implant and, on the end face 5, it forms a spacer, which fixes the implant in the shape shown in FIG. 4, in which the one-piece plastic part that forms the sidepieces 12,13 and the web 14 is elastically deformed.

At its end facing the bore 15, the slider 19 could have recesses or projections that are suitable for engagement by a tool, so that the slider can be retracted from the position shown in FIG. 4, e.g., to release the implant and reposition it between the vertebrae.

A tool for exposing cancellous tissue in the regions of the vertebra opposite the opening 10 can also be guided through the bore 15. The cancellous tissue then forms new bone tissue that infiltrates the opening 10.

In the state shown in FIG. 4, the teeth 18 penetrate the compact tissue resting against the implant, which securely locks the implant in place between the vertebral bodies.

It is advantageous for the teeth 18 to be positioned as far as possible from the vertebral canal and from the main load-bearing axis of the spine, so that the penetration of the bony tissue neither damages nerve pathways nor impairs the load-bearing capacity of the spine.

In the embodiment shown in the drawings, the height of the implant at the end face 5 in the spread state is as great as at the opposite end face 6. However, the outside surfaces of the sidepieces facing the vertebral bodies could also be designed in their thickness profile in the longitudinal direction of the implant in such a way that the height of the implant in the spread state is greater or smaller at the end face 5 than at the end face 6 to allow adaptation to vertebrae that are inclined towards each other, especially in the lumbar region of the spine.

The slider 19 can also have a bore that opens towards the longitudinal sides 3,4 for holding another metal pin arranged perpendicularly to the metal pin in the bore 17. In this way the spatial position of the implant can be accurately judged from the two high-contrast pins appearing in the radiograph.

The openings 9 and 10, which serve to guide the slider 19, may become infiltrated by bony tissue after the implantation, so that the implant becomes largely embedded in bony tissue connecting the vertebrae with each other.

The invention is not limited by the embodiments described above which are presented as examples only but can be modified in various ways within the scope of the protection defined by the appended patent claims.

What is claimed is:

1. An implant for placement between vertebrae, comprising: two sidepieces joined together at one end and free at another end, each of the sidepieces being placeable against one of the vertebrae; a device for vertical distraction of the sidepieces, outside surfaces of the sidepieces that face the vertebrae and at least stages of inner surfaces of the side pieces being configured to converge towards the free ends of the sidepieces in an initial position for the distraction; and a spreading element arranged between the sidepieces for spreading apart the sidepieces, wherein the spreading element is a slider mounted so as to be capable exclusively of translatory motion and wherein, in a spread-apart state of the sidepieces, the slider rests against the sidepieces over an entire horizontal width thereof, and wherein, for spreading apart the sidepieces, the slider is movable from a location where the sidepieces are joined together toward the free ends of the sidepieces, wherein the slider locks in an end position in which the sidepieces are spread.

2. The implant in accordance with claim 1, wherein the slider locks releasably in the end position.

3. The implant in accordance with claim 1, wherein the slider is flush with an outer surface of the implant in an end position in which the sidepieces are spread.

4. The implant in accordance with claim 1, wherein the implant is configured for placement in a lateral half-space between two vertebrae together with another implant, which shows mirror symmetry with respect to the first implant and is placeable in the other half-space.

5. The implant in accordance with claim 1, wherein the implant has a vertical opening formed as an oblong hole in which the slider is guided.

* * * * *